United States Patent [19]
Block et al.

[11] Patent Number: 5,424,545
[45] Date of Patent: * Jun. 13, 1995

[54] NON-INVASIVE NON-SPECTROPHOTOMETRIC INFRARED MEASUREMENT OF BLOOD ANALYTE CONCENTRATIONS

[75] Inventors: Myron J. Block, P.O. Box 148, North Salem, N.H. 03073; Lester Sodickson, Waban, Mass.

[73] Assignee: Myron J. Block, North Salem, N.H.

[*] Notice: The portion of the term of this patent subsequent to Jan. 14, 2011 has been disclaimed.

[21] Appl. No.: 182,572

[22] Filed: Jan. 14, 1994

Related U.S. Application Data

[63] Continuation-in-part of Ser. No. 914,265, Jul. 15, 1992, Pat. No. 5,321,265, and Ser. No. 130,257, Oct. 1, 1993.

[51] Int. Cl.$^6$ ............................................. G01N 21/35
[52] U.S. Cl. ................................. 250/343; 356/405
[58] Field of Search .............. 250/343, 339, 340, 341, 250/343; 356/405

[56] References Cited

U.S. PATENT DOCUMENTS

| | | | |
|---|---|---|---|
| 4,178,917 | 12/1979 | Shapiro | 128/665 |
| 4,278,538 | 7/1981 | Lawrence et al. | 209/580 |
| 4,286,327 | 8/1981 | Rosenthal et al. | 364/498 |
| 4,520,265 | 5/1985 | Griggs et al. | 250/338 |
| 4,543,481 | 9/1985 | Zwick | 250/339 |
| 4,641,973 | 2/1987 | Nestler et al. | 356/418 |
| 4,655,225 | 4/1987 | Dähne et al. | 128/633 |
| 4,799,795 | 1/1989 | Fateley | 356/310 |
| 4,850,365 | 7/1989 | Rosenthal | 128/664 |
| 4,882,492 | 11/1989 | Schlager | 250/346 |
| 4,928,014 | 5/1990 | Rosenthal | 250/341 |
| 4,975,581 | 12/1990 | Robinson et al. | 250/339 |
| 5,028,787 | 7/1991 | Rosenthal et al. | 250/341 |
| 5,054,487 | 10/1991 | Clarke | 128/633 |
| 5,070,874 | 12/1991 | Barnes et al. | 128/633 |
| 5,321,265 | 6/1994 | Block | 250/343 |

FOREIGN PATENT DOCUMENTS

233873 3/1986 German Dem. Rep. .
1187032 11/1985 U.S.S.R. .
WO88/01128 2/1988 WIPO .

OTHER PUBLICATIONS

Willard et al, "Instrumental Methods of Analysis" D. Van Nostrand Co. p. 852, (1981).

Cavinato et al., "Noninvasive Method for Monitoring Ethanol in Fermentation Processes Using Fiber-Optic Near-Infrared Spectroscopy" *Anal. Chem.*, vol. 62, pp. 1977–1982, (1990).

Bohlke et al., "A new stationary Hadamard encoding masks for near-infrared Hadamard transform Raman spectrometry" *Journal of Molecular Structure*, vol. 247, pp. 293–303, (1991).

Dyer et al., "A Fast Spectrum-Recovery Method for Hadamard Transfrom Spectrometers Having Nonideal Masks" *Applied Spectroscopy*. vol. 43, No. 3, pp. 435–440, (1989).

(List continued on next page.)

*Primary Examiner*—Paul M. Dzierzynski
*Assistant Examiner*—Richard Hanig

[57] ABSTRACT

A new non-invasive non-spectrophotometric method for measuring the blood concentration of analytes such as glucose has been developed. The apparatus and methods of the invention exploit analogies with colorimetry and color perception to extract concentration measurements from the global structure of the intensity versus wavelength absorbance or transmission profile. A plurality of broad spectrum filters transmit distinguishably coded beams of radiation in overlapping portions of the spectrum to the sample. Radiation reflected or transmitted by the sample is detected and decoded. LED's may be used instead of the broad spectrum radiation generating device and the filters. Further, a scanning interferometer can be used as the illuminating and coding device. In a preferred mode, congruent illumination is utilized. The coded signals are analyzed by analogy to colorimetry and visual processing and can be converted into concentration measurements.

115 Claims, 8 Drawing Sheets

OTHER PUBLICATIONS

Brochure–Minolta Chrome Meter CR–200.

Dufort and Lumsden, "Color categorization and color constancy in a neutral network model of V4", *Biol. Cybern.*, vol. 65, pp. 293–303, (1991).

Rubner and Schulten, "A Regularized Approach to Color Constancy", *Biol. Cybern.*, vol. 61, pp. 29–36, (1989).

Schmitt, "Simple Photon Diffusion Analysis of the Effects of Multiple Scattering on Pulse Oximetry", Abstract, *IEEE Transactions on Biomedical Engineering*, vol. 38, No. 12, p. 1194, (1991).

Wukitsch et al., "Pulse Oximeter: Analysis of Theory, Technology, and Practice", *J. clin. Monit.*, vol. 4, pp. 290–301, (1988).

Moore et al., "A Real-Time Neural System for Color Constancy", Abstract, *IEEE Transactions on Neural Networks*, vol. 2, No. 2, (1991).

NON-INVASIVE NON-SPECTROPHOTOMETRIC INFRARED MEASUREMENT OF BLOOD ANALYTE CONCENTRATIONS

REFERENCE TO RELATED APPLICATIONS

This Application is a Continuation-in-Part U.S. patent application Ser. No. 914,265, filed Jul. 15, 1992, U.S. Pat. No. 5,321,265, entitled: "Non-invasive Testing", the disclosure of which is incorporated herein by reference. This Application is also a Continuation-in-Part to U.S. patent application Ser. No. 130,257, entitled: "Improvements in Non-Spectrophotometric Measurement of Analyte Concentrations and Optical Properties of Objects," filed Oct. 1, 1993, the disclosure of which is also incorporated herein by reference.

BACKGROUND OF THE INVENTION

The present invention relates to the measurement of the concentration of constituents of interest using radiation, preferably near infrared radiation. More particularly, an improved apparatus has been developed which utilizes a method of measuring the concentration of constituents such as glucose, alcohol, hemoglobin and its variants such as deoxyhemoglobin, myoglobin, and other reduced or substituted forms of hemoglobin or heme-group containing molecules, drugs of abuse or other clinical analytes in a non-invasive manner. Because the apparatus and method do not require a finger puncture to obtain a blood sample, they are particularly suitable for home glucose testing.

With the spread of AIDS, and the associated fear among the public and health care personnel of contracting the disease, development of testing methods that do not require invasive procedures, including the taking of blood samples, has become an important goal. Not only AIDS, but other diseases such as hepatitis may be spread through invasive procedures if adequate precautions are not taken. For example, a recent article, "Nosocomiel transmission of Hepatitis B virus associated with the use of a spring-loaded finger-stick device," *New England Journal of Medicine* 326 (11), 721–725 (1992), disclosed a hepatitis mini-epidemic in a hospital caused by the improper use of an instrument for taking blood samples. The article describes how the nurses were unintentionally transmitting hepatitis from one patient to another with the sampling device itself. This type of disease transfer is eliminated by non-invasive testing.

Effective management of diabetes has also given rise to the need for non-invasive testing instruments. Many diabetics must measure their blood glucose levels four or more times a day. Instruments currently used for in-home glucose testing require a painful finger prick to obtain a blood sample. Although the price of these instruments has dropped considerably, such testing requires the use of disposable materials that can be cumulatively costly. Further, the discomfort, inconvenience, and health risks associated with frequent puncture bleeding are considerable.

Accordingly, a number of groups have recently tried to make non-invasive instruments for measuring the concentration of various analytes, particularly blood glucose. Much of the recent development work in non-invasive testing has been exploring the use of the near infrared spectral region (700–2500 nm). This region contains the third overtones of the glucose spectrum and its use eliminates many of the interference bands that cause potential problems for detection. However, substantially all of this work has been carried out using classic spectrophotometric methods. These methods use a set of narrow wavelength sources and a broad wavelength response detector (Rosenthal), a broad wavelength source and narrow wavelength response detectors (Sandia), or scanning spectrophotometers which scan wavelength by wavelength across a broad spectrum. The data obtained with these methods are spectra which require substantial data processing to eliminate (or minimize) the background. Accordingly, the relevant papers are replete with data analysis techniques utilized in an attempt to extract the pertinent information. Examples of this type of testing include the work by Clarke, see U.S. Pat. No. 5,054,487, and the work by Rosenthal et al., see, e.g., U.S. Pat. No. 5,028,787. Although the Clarke work uses reflectance spectra and the Rosenthal work uses primarily transmission spectra, both rely on obtaining near infrared spectrophotometric data.

One problem with all such methods is that spectrophotometers were conceived primarily for accurate wavelength-by-wavelength measurement of spectral intensities. Where, as in non-invasive measurement of the concentration of glucose and other clinical materials, the analyte of interest has weak broadband spectral features and is present in a mixture containing other substances with substantially overlapping broadband spectral structure, use of classical spectrophotometric methods employ substantial, and ultimately unsatisfactory, data analysis in an attempt to extract the desired concentration from a background of interfering signals. One basic principal of all measurement is, however, that the measurement step determines the information content of the data, and that computation or transformation adds no new information. In other words, no amount of analysis can make up for the fact that the distinguishing features of the spectra of the analytes of interest are not the sharp spectral peaks of classical spectrophotometry but rather are broad and shallow structures. The analyte is identifiable not by the location of its spectral peaks, but by the global structure of its intensity versus wavelength structure. Since spectrophotometers are not designed to generate this kind of information, they are ill-suited for measurements of this type.

The spectra of the analytes of interest, consisting of a few weak low resolution features, with overlapping backgrounds, are reminiscent of the spectra of reflected, emitted, or transmitted light from colored objects in the visible. The human visual system, while an incompetent spectrophotometer, is superb at the subtlest color discrimination and identification, even under greatly varying illumination conditions. Therefore, the present invention draws on an analogy with the discrimination of colored objects by the eye, rather than classic spectrophotometric measurements, to obtain data. Because of its greater penetration of tissue, the preferred spectral region for testing is the infrared.

Many related but distinct approaches are possible in developing an apparatus and a method for measuring the concentration of an analyte of interest by exploiting the analogy to color perception in the visible. The primary approach is to illuminate the object with broadband radiation, the analog of white light in the visible, and to use a series of spectrally overlapping filters to detect the reflected, emitted or transmitted radiation to determine the object's relative "color." This approach is disclosed in U.S. patent application Ser. No. 914,265, the disclosure of which is incorporated herein by reference. Similarly, U.S. patent application Ser. No. 130,257, the disclosure of which is also incorporated herein by reference, concerns a number of modifications and improvements on the basic method and apparatus disclosed in application Ser. No. 914,265. The present application concerns further modifications and improvement on the methods and apparatus described therein to obtain even better data. In fact, many of these methods are useful even in classic spectrophotometric systems.

While visual perception is very complex and not completely understood, significant progress has been made recently. For example, one recent article, "Color categorization and color constancy in a neural network model of V4," *Biological Cybernetics* 65,293–303 (1991) describes the simulation of neurons which mix the signals from the three types of visual cones to mimic the ability of the retina and region V4 of the cerebral cortex to respond preferentially to particular colored stimuli, and to disregard changes in the illuminant in the identification of the color of objects in a multi-colored scene. The latter feature is called color constancy. A related article, "A Real-Time Neural System for Color Constancy," *IEEE Transactions on Neural Networks*, Vol. 2, No. 2, March 1991, describes the hardware implementation of a number of color constancy algorithms based on Land's Retinex theory to improve the ability of a TV system to produce true-color images under varying illumination conditions, the disclosure of which is incorporated herein by reference. One feature of the models which leads to the improvements is the mixing of spatial variations between a given cone and other adjacent ones in its so-called surround region.

One approach for relating the concentration of an analyte to absorption or reflection in the infrared is to obtain and process the raw data as closely as possible to the known aspects of color perception, utilizing a succession of steps or processing levels. Each step provides a useful product and succeeding steps represent products of greater capability.

The first step to achieve accurate information is the simple analog of a colorimetry approach. Colorimetry is numerical color communication in which three dimensions are used to describe the color. It is the trivalent nature of color vision that permits color to be specified in a three dimensional space.

There presently are several such three dimensional colorimetry spaces in use. One of these spaces is the CIE 1931 (x, y)-chromaticity diagram, shown in FIG. 1*b*, which shows hue and saturation values. Luminosity, the third dimension, is not shown in FIG. 1*b* but would be in a Z-direction. FIG. 1*a* shows the standard observed spectral responses used to generate FIG. 1*b*.

Another colorimetric space, described in terms of hue, chroma, and value, is shown in FIG. 2. This solid can be described as the three numerical values which can specify any perceived color.

It is important to note that although it is convenient to describe color in terms of colorimetry, this is not true color perception which is much more complex. However, colorimetry is useful for color matching under specific conditions. An analog of colorimetry, particularly one in the infrared region, would show similar usefulness in determining analyte concentration.

There are commercially available colorimeters in the visible for measuring tristimulus values in terms of luminosity, hue and saturation, yielding numerical values such as are illustrated by FIG. 1. Briefly, these colorimeters use three detectors, with each detector input being filtered with a different filter function. Each of the filter functions and detector responses are chosen to be similar to the three absorption spectra of the pigments of the three color receptive cones of the human retina. It appears that no one other than the present inventors have previously used, or even considered the use of, an analog of color perception for wavelength expanded colorimetry for concentration measurements or even applied the method of colorimetry to infrared measurements as described herein.

In addition to non-invasive blood measurements for constituents like glucose, the system could replace present pulse oximeters. Non-invasive measurement of arterial oxygen saturation by pulse oximetry is widely acknowledged to be one of the most important technological advances in clinical patient monitoring. Pulse oximeters measure differences in the visible and near infrared absorption spectra of fully oxygenated and reduced hemoglobin in arterial blood. Unlike clinical blood gas analyzers, which require a sample of blood from the patient and can only provide intermittent measurement of patient oxygenation, pulse oximetry provide continuous, and instantaneous, measurement of blood oxygen levels.

However, current commercial oximeters, and their algorithms are inaccurate under conditions of low pulse pressure and/or low oxygen saturation. These severe conditions are observed in the normal unborn fetus or where the features of interest are broad. Unlike the transmission sampling of the commercial oximeters, space limitations associated with the fetus require that the spectral data be obtained by reflectance sampling. It has been suggested that a new analysis technique using multivariate calibration methods can improve the precision, accuracy and reliability of quantitative spectral analysis. Even these techniques are limited by the type of input data.

The apparatus and methods of U.S. patent application Ser. No. 914,265 solves this problem by providing infrared analogs of colorimetry. While the data provided is better than that from spectrophotometers, signal-to-background can always be improved, thereby providing even greater sensitivity.

Further, one problem common to all optical non-invasive test systems is improper readings due to stray or extraneous radiation. A system which eliminates or minimizes this problem has particular advantageous properties for the noncontrolled setting such as home glucose monitoring.

Accordingly, an object of the invention is to provide an apparatus which provides an improved measure of the concentration of a constituent of interest in a sample using the infrared analog of colorimetry.

Another object of the invention is to provide an improved method of accurately, inexpensively, and quickly measuring the concentration of clinical analytes in a non-invasive manner using an analog of colorimetric analysis.

A further object of the invention is to provide an improved apparatus for and a method of non-invasive concentration measurements using the analog of colorimetry that allows for convenient sample insertion and removal while minimizing responsive to radiation from extraneous sources.

A still further object of the invention is to provide an apparatus for and a method of non-invasive determinations of the concentration of an analyte of interest in a mammalian bloodstream with an improved signal-to-background level.

A still other object of the invention is to use a scanning interferometer to provide the illuminating and coding source in the method of the invention.

These and other objects and features will be apparent from the description and the accompanying drawing.

SUMMARY OF THE INVENTION

The present invention features an improved apparatus and methods for carrying out testing for concentration of a constituent of interest in a sample, preferably in a non-invasive manner. The present invention also has utility in determining the optical properties of an object. The apparatus and methods use reflectance or transmission measurements, particularly in the near infrared.

U.S. patent application Ser. No. 914,265 discloses an apparatus which uses, and expands upon, an analog of human vision to develop data, in a non-invasive manner, which is much improved from that available through classical spectrophotometric measurements. U.S. patent application Ser. No. 130,257 disclosed a series of improvements to the basic concept disclosed in application Ser. No. 914,265. These improvements were directed to a variety of means of improving signal-to-background in the measurement process. In its various embodiments, the apparatus and method of the present invention provides further improvements both to the basic and improved methods and apparatus described in the aforementioned patent applications. These improvements provide rapid, inexpensive measurements of high accuracy and are particularly adapted for non-invasive testing of the human body for constituents such as glucose, hemoglobin in its various forms, or drugs of abuse. These improvements allow better standardization and the use of the basic invention in circumstances where the more simplified apparatus might not provide meaningful data.

The basic concept described in the aforementioned patent applications was that by using broadband illumination of a sample and detecting the transmitted, emitted, or reflected radiation using broadband detectors having at least partial overlapping response, an analog of human color vision could be obtained and more meaningful data would be generated. The improvements described in the second patent application included "congruent sampling," a means for insuring that each of the plurality of detectors receives radiation from substantially the same portion of the sample transmitted (or reflected) in the same direction so that all the rays emerging in all directions from each point of the sample are incident in the same direction on each detector. In a congruent sampling system, the detectors are superimposable; that is, if a transformation (or translocation) was made from the position of one detector to the position of another detector, the identical optical sampling is achieved. Congruent sampling guarantees that the optical beam path from the sample to each detector is both of equal length and equal angles, thereby eliminating a substantial portion of error caused by viewing from unequal distances and angles. Other described improvements included using arterial pulse sampling, comparing data using different portions of the same sample or different wavelengths to generate different but parallel data sets with different but not superimposable backgrounds, and using a filter with spectral structure in connection with one or more detectors. Each of these improvements, or logical variants thereof, can be used with the present invention.

The present invention uses the basic concept of the aforementioned applications but with a different variation; a plurality of radiation sources or beams (as compared to a plurality of detectors), each such source covering a distinct portion of the spectrum (but with at least partial overlap with the other beams) is used. Each of the beams has identifying information coded thereon which allows the detector (or plurality of detectors) to identify a particular beam and thus the transmittance or reflectance by the sample.

In more detail, the invention provides an apparatus for measuring the concentration of a constituent of interest which has absorbance or reflectance bands in a selected portion of the spectrum, preferably the near infrared. The apparatus includes a plurality of sources or beams of broad-band infrared radiation for illuminating a sample. In some embodiments of the invention, the plurality of sources is obtained from a single broad spectrum radiation emitting source using beam splitters or a bundle of optical fibers. In another aspect, the plurality of beams is provide by LED's (light emitting diodes) selected such that there is at least partial overlap in wavelength emission characteristics. In still a further embodiment, the radiation emitted by a broad spectrum radiation source, first transmitted through a scanning interferometer, is used.

The apparatus also includes coding means for placing an identifiable, distinct code on the radiation from each of the sources. If the interferometer is used, this provides the coding as well. The coding is achieved by known methods such as separately modulating the radiation from each source. In a preferred embodiment of the invention, the radiation from each source is modulated by passage through choppers that time vary the amplitude of the radiation from each source. The frequency of such modulation is different for each source so that the radiation from each source is distinguishable from that of all the other sources. If LED's are used, the coding or modulation can be achieved by turning the sources on and off at a desired frequency or at unique phases within a common frequency (e.g., 10 khz), with the coding being different for each source.

In one preferred embodiment, radiation from a single source is split into the plurality of beams. A similar effect can be achieved by using a plurality of radiation sources, assuming that their output is substantially identical or that together they cover the whole spectrum of interest, with overlap in wavelength. This apparatus is arranged so that each beam of radiation impinges on one and only one of a plurality of broad bandpass optical filters, each of which transmits radiation in a predetermined portion of the spectrum. The term "broad bandpass optical filter", as used herein, means a filter that allows for significantly overlapping transmission. In effect, each filter transmits radiation that is substantially confined to a portion of the infrared spectrum. A preferred embodiment of the invention has at least three such filters with different but mutually overlapping spectral transmissions which are an infrared analog of the primary responses of the retinal cones. A "black-white" type filter (or a plurality of them) which passes all radiation in the region of interest, and acts as an analog of rod vision may also be used. The beam may be coded or modulated either before or after passing through the filters.

If LED's or an interferometer is used as the illuminating source, the broad bandpass filters before the sample are normally unnecessary. If LED's are used to generate the plurality of beams, they themselves can be electrically modulated to produce the coded beams and act both as the modulated radiation sources and the band selecting filters. If the interferometer is used, it codes every wavelength passing through it with a unique temporal frequency, and broad bandpass electrical filters are used after the sample.

The apparatus also includes means for combining the distinguishable temporally coded beams of infrared radiation to produce an effective single beam of radiation. This could be carried out by bundling optical fibers for the illuminating radiation or by some lens or reflectance system. Preferably, the radiation sources are arranged so that "congruent illumination" is achieved. Congruent illumination is the analog of congruent sampling described previously. In congruent illumination, each radiation source is arranged such that the sample receives illuminating radiation from each source along the same pathlength and same angles, so the sources are superimposable. This can be achieved using beam splitters, mirrors, and other similar devices to allow plural sources and/or filter location, or using optical fibers. The apparatus further includes a sample chamber on which this single beam impinges. The sample chamber can be arranged for non-invasive measurements of a portion of the human body such as a finger.

After interacting with the sample, the infrared radiation transmitted or reflected by the sample is detected by at least one detector responsive to the intensity of the radiation transmitted (or reflected) by the sample. In one embodiment of the invention, the detector is a standard silicon photocell. Using techniques well-known in the art, the detected signal is decoded to distinguish the portion of the intensity originating from each source. Narrow bandpass electrical filters are a preferred decoding means, whereby the filter response is centered about the coding frequency; e.g., the chopper frequency. The response from the detector unit is in the form of an output signal which is transmitted to analysis means for combining and converting the output signal into a measure of the concentration of the constituent of interest.

In certain instances, it is advantageous to replace the single detector with a linear or two-dimensional array of detectors. In this case, the individual detectors in the array do not necessarily have to be congruent to each other; they may receive the mixed and coded beams of light entering the tissue from the congruent launch point through different paths through the tissue. At each detector however, the intensity arising from each of the individual sources is identified, and, the "color" analog constructed. With a two-dimensional array, the infrared equivalent of a color TV image is obtained: this allows the comparison of the varying "color" across the image to achieve an infrared analog of "color constancy" in mammalian color vision. This embodiment is a higher dimensional equivalent of the two finger approach described in application Ser. No. 130,257, in which incoherent background signal contributions are minimized by the coherent addition of "color" information across the image.

If the interferometer is used as the radiation source, the coding takes place in the interferometer itself, so that each wavelength is separately coded with a different identifying code such as a different harmonic frequency. Here, the radiation on the finger is in the form of an interferogram. The output of the detector would not go to a Fourier transformer as in classic FTIR but rather to a parallel set of broad bandpass electrical filters, each of whose frequency passbands have at least one region of overlap with the passband of another filter. Preferably, these broad bandpass electric filters include an integrator which integrates the signal over the width of the frequency passband. The output of the signal is processed similarly to the outputs from any of the other illuminating/modulating/decoding methods previously described.

One key to the present invention is the realization that the system measures samples with an analog of color perception. Color perception is the color response of the eye mixed in a neural net. The color response of the eye is mediated by the overlapping response of the three different types of retinal cones, with the peak responses in the short-, mid-, and long-wavelength portions of the visible spectrum.

The color constancy capability of color perception is not now employed in colorimetry. Therefore, present colorimetry measurements vary with the color of the source of illumination. The present invention removes this limitation.

The simplest approximation of color perception for certain specific conditions is colorimetry. A near infrared analog of colorimetry, using infrared rather than visible radiation, is proposed herein, as is the use of colorimetry for concentration measurements and improved analysis methods. Accordingly, preferred embodiments of the invention have at least three beams, each having a spectral illumination range centered about a different portion of the selected spectrum but with bands sufficiently wide that there is some overlap with at least one, and preferably more than one, other of the illumination units. The radiation or beam generation means may also include a black-white or luminosity illuminator which generates entire spectrum for which the other illumination units have a spectral output.

The use of distinguishably coded "colored" beams and the simultaneous decoding and processing of the detected signal offer certain advantages. In particular, any detected signals that are not modulated at one of the chosen modulation frequencies are effectively eliminated from the signal processing stage.

The next step in complexity is to more closely approach color perception by using computational methods operating on the outputs of the decoder to emphasize the analyte with respect to the background. As a start, the computational models of color vision that have been developed in the field of "artificial intelligence" for attempting to achieve machine color vision will be utilized. While this form of data processing can increase accuracy and discrimination from background, as in any of these systems, the manner in which the data is collected is more important than the manner of processing since the processing methods do not add information.

In this approach to an analog of human color perception, the decoder outputs are fed into a neural network assembled similarly to the neural organization circuitry of the retina and region V4 of the visual cortex of the brain (i.e., the brain's color processing center). Here, learning by the circuitry is used for a variety of uses including detection, quantification, and in particular signal discrimination against background, with a smaller component cost and small size. Neural networks, in the form of chips and other hardware, are presently available. Neural networks (or nets) provide processing which is similar to the brain (albeit on a less complicated scale) and, as such, can be "taught" to eliminate certain items of background.

The apparatus (and methods) can be adapted for detection of many substances. Obvious choices for applicability of the invention include glucose, glucose indicating constituents, cholesterol, lipids, hemoglobin and its variants and alcohol and drugs of abuse or indicating constituents thereof. For purposes of the invention, it does not matter whether the glucose or drug of abuse is measured directly but rather solely that the measurement of the sample can be correlated to the concentration of the constituent of interest. For example, it may be that the glucose is always correlated with the presence of a particular carrier or other indicating constituent and the carrier or constituent is measured in addition to and/or instead of the glucose itself. Any analyte with absorption bands in the response range of the apparatus can be used. Further, the apparatus can be used to measure water bands as well as the constituent of interest, thereby facilitating the determination of concentration. The constituent may shift the water bands towards its color which can provide the indicating activity even if the bands of the constituent itself are indistinct; that is, the fractional shift of the water bands may present the sought information.

The invention also features a method for measuring the concentration of a constituent of interest which absorbs or reflects light. The method has the steps of illuminating the sample with radiation in a plurality of beams constituting partially overlapping portions of a selected region of the spectrum, preferably the near infrared, and detecting transmitted or reflected radiation from the sample. The radiation from each of the portions is distinguishably coded prior to impinging on the sample, preferably using modulation as provided by choppers and decoded subsequent to impinging on the sample; e.g., by using narrow bandpass electrical filters centered about the coding frequencies. At least one signal corresponding to the detected radiation is generated and analyzed to determine the concentration of the constituent of interest.

A plurality of beams, preferably covering at least three partially overlapping regions of the infrared, are selected using broadpass optical filters, in analogy to the three retinal cones. Decoding the radiation of the various "colors" reflected or transmitted by the sample in such a case allows analysis such that the output is formed into an analog of colorimetric (e.g., tristimulus) values. In another aspect of the invention, the analysis may use an analog of a neural network, paralleling the working of the eye and brain. This neural net based apparatus may be used to provide a degree of independence from color variations in the effective illuminant.

In one preferred embodiment, this is accomplished by the use of an array of spatially displaced detectors whose "tristimulus" readings are mixed to obtain the illuminant independent (i.e., color constant) value of the "color" of the analyte of interest. As light traverses tissue, the effective illuminant color changes with depth as a result of scattering and absorption by background constituents. The analyte concentration is relatively invariant while the background induced changes in illumination varies significantly as the path length changes. The spatially displaced detectors sample different path lengths through the tissue, allowing congruent addition of the analyte information, while the variable background effects on the illuminant are reduced or averaged out. The performance of the system is further improved by use of more than three primary cone responses; i.e., by carrying the analogy into higher dimensional color spaces.

The method of the invention is particularly well suited to non-invasive testing for a constituent found in the human body such as glucose, a glucose indicator, or a drug of abuse. The finger is the preferred region for non-invasive testing.

Another aspect of the invention is the use of paired detectors for referencing. In present non-invasive methods, there is no way to obtain a control reporting a "zero" concentration of the constituent of interest. However, by using a simulating filter or a filter made of the same material as the analyte but which has a concentration of the constituent of interest that is much higher than that in the sample, changing amounts of constituent in the sample merely cause a minor perturbation in the measurements from that "high concentration" reference detector. It may also be possible to use a material with substantially identical absorbance (or reflective) characteristics in place of the high concentration filter. One example of this is using a chamber filled with a high glucose concentration as a "glucose filter."

By using paired detectors with the "high concentration" filter in front of one detector of the pair, one can obtain background measurements, unperturbed by the presence of the analyte, to enhance discrimination and also to provide a reference signal to implement color constancy. The term "paired detectors," as used herein means two or more detectors which are identical except for the high concentration filter. For example, there could be paired red analog detectors, paired green analog detectors and paired blue analog detectors, with the only difference being the addition of the high concentration filter to one of each pair. This type of high concentration filter is not limited to use with the apparatus and methods described previously but has general applicability to any radiation detecting system.

The following detailed description and the drawing will more clearly delineate the invention.

DETAILED DESCRIPTION OF THE INVENTION

The present invention provides improved non-invasive procedures for measuring the concentration of a constituent of interest that has absorbance, emittance, or reflectance bands in a selected region of the electromagnetic spectrum, preferably 500–10,000 nm, most preferably 700–2500 nm. This invention can be used to determine optical properties of a sample or object in addition to making concentration measurements. The apparatus and methods are improvements to the basic concept described in U.S. patent application Ser. No. 914,265 and the improvements described in U.S. patent application Ser. No. 130,257. The apparatus and methods of the prior applications are based, in part, on the recognition that present problems associated with non-invasive concentration measurements that use radiation as a probe relate to the type of information that is obtained, e.g., from spectrophotometers, rather than the processing of the information itself.

Although using different analysis techniques can clarify what information has been obtained, these analysis techniques cannot generate results better than the underlying information obtained. By applying an analog of color perception to concentration measurements, particularly by forming a multi-dimensional near infrared parallel of the three different pigments of the cones of the retina, significantly better information relating to concentration can be obtained. Since in color perception "color constancy" is maintained under extreme variations in illumination, the use of neural networks or digital computation to process information in a manner more similar to the information processing of the eye-brain is preferred. Color constancy is the capacity to successfully recover the reflected, emitted, or transmitted color of an object regardless of the composition or intensity of the ambient illuminating radiation. A further description of color constancy is found in Dufort and Lumsden, "Color categorization and color constancy in a neural network model of V4", *Biol. Cybern.* 65,293–303(1991), the disclosure of which is incorporated herein by reference.

The improvements herein to the basic invention set forth in the aforementioned patent applications concern improved means of obtaining data such that the signal desired is maximized and the background signal (or noise) is minimized. The embodiments described herein provide alternate means to achieve this same advantage. In fact, a preferred apparatus could have a combination of several of these embodiments used in concert.

Figure 1A:
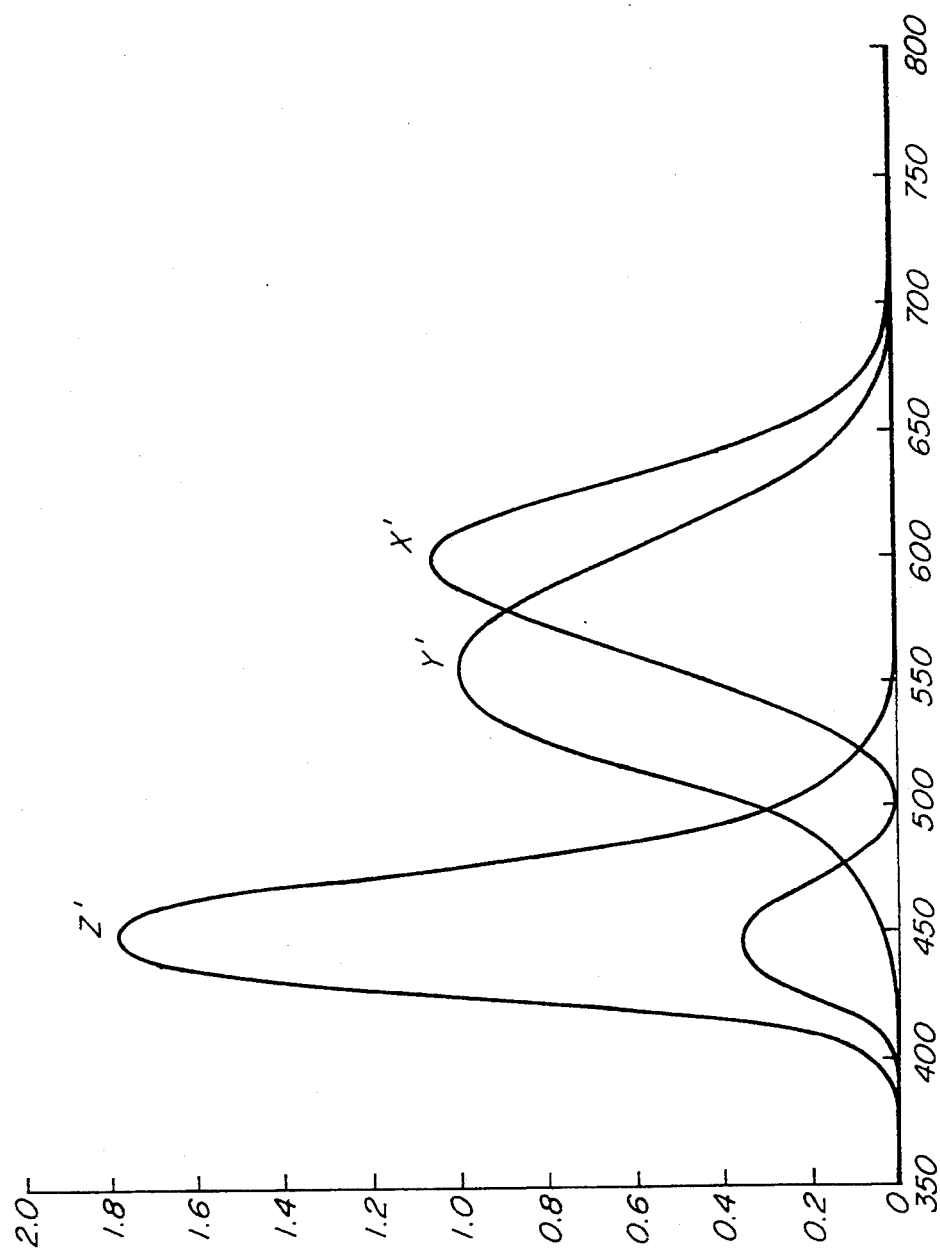
FIG. 1 shows the CIE 1931 chromaticity plot, shown in standard spectral tristimulus values (FIG. 1a) and normalized form (FIG. 1b)
Figure 1B:
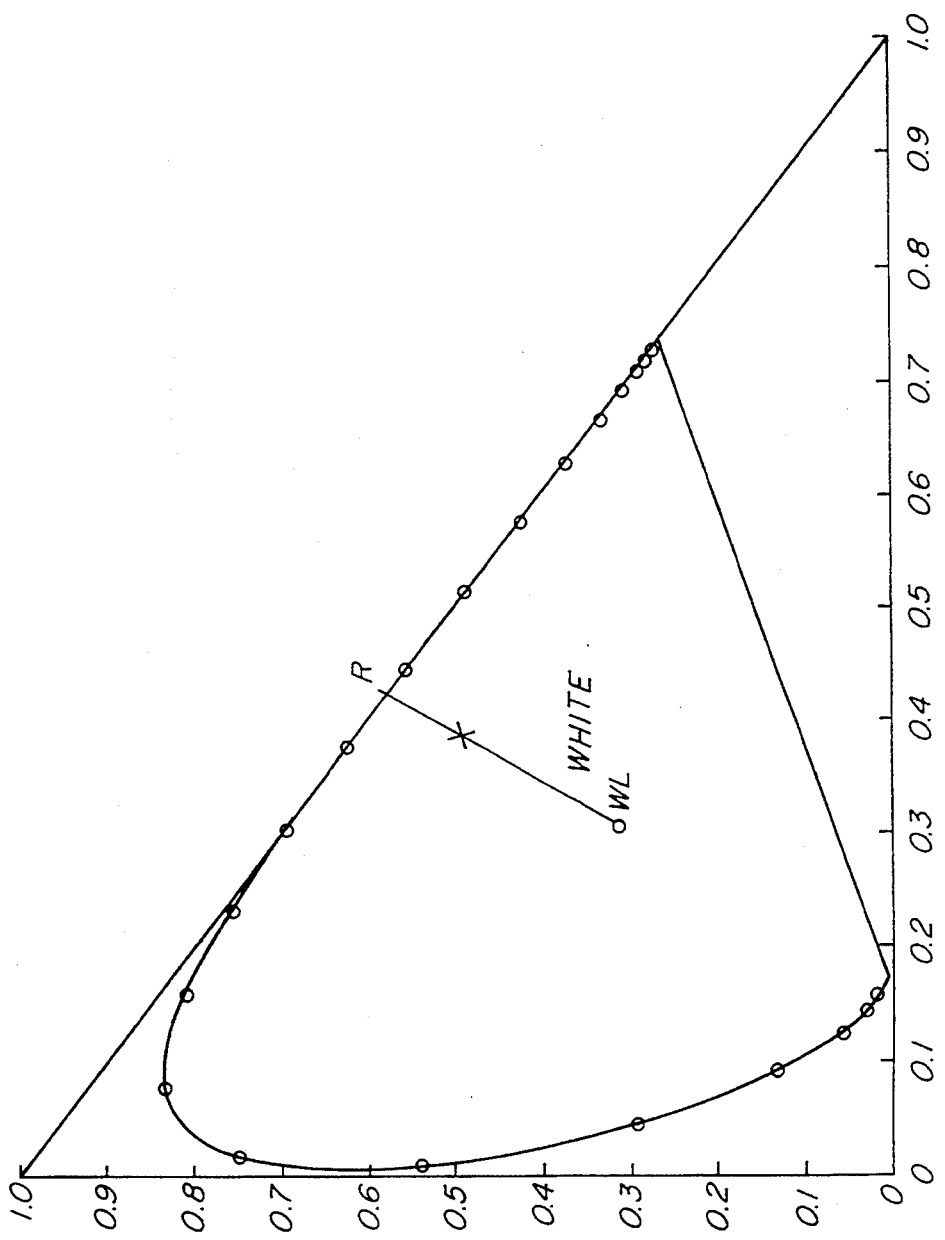
Figure 2:
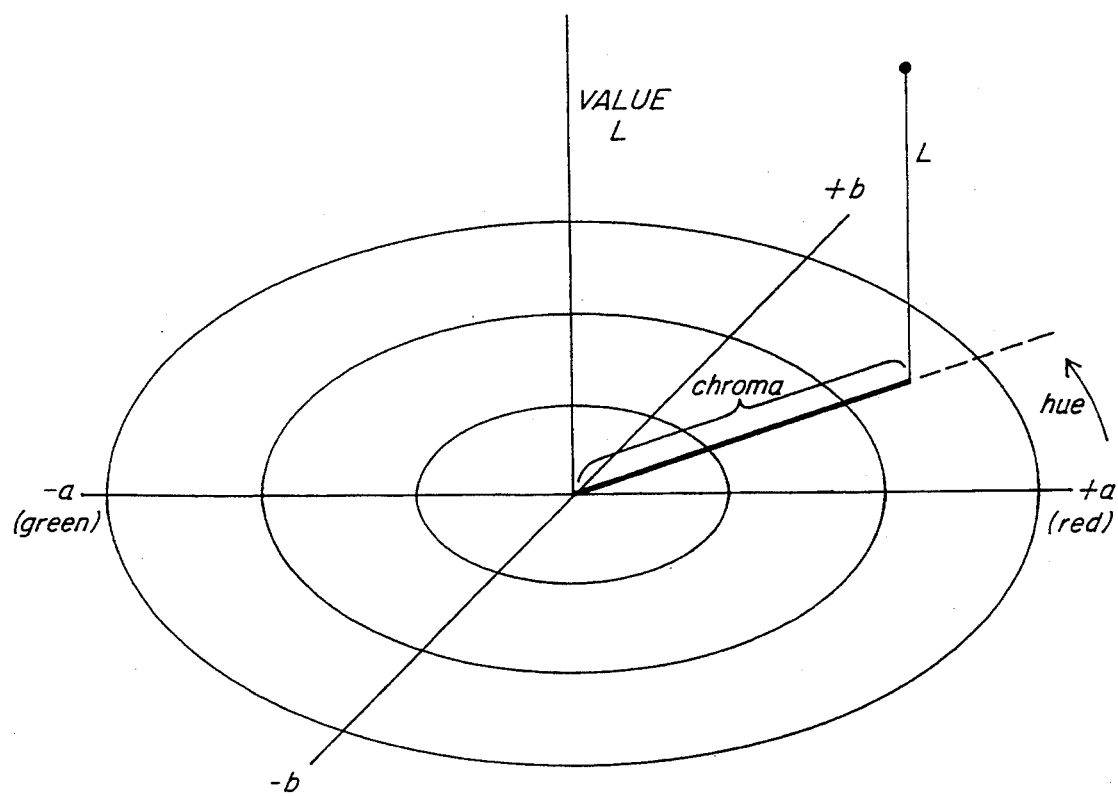
FIG. 2 is a three dimensional plot of color in terms of hue, chroma and value.

FIGS. 1 and 2 show different ways of handling data in classic instrumental colorimetry. FIG. 1a shows the CIE 1931 standard color matching functions, which approximate the spectral response of the three types of cones in the human retina. FIG. 1b, a so-called chromaticity plot, is a convenient two dimensional representation of the systematic variation of this standard observer to monochromatic light of different wavelengths. Each point on the continuous curve in FIG. 1b is plotted as a normalized (X, Y) pair, where the values are obtained from the three response curves in FIG. 1a by dividing by the sum of all three response, according to the formulas:

$$D = x' + y' + z' \quad X = x'/D \quad Y = y'/D \quad Z = z'/D$$

This normalization lead to the result $X+Y+Z=1$ and completely defines the relative values of X, Y, and Z. Accordingly, specification of X and Y on the two dimensional plot in FIG. 1b is sufficient to specify Z as well. Monochromatic light passes at the indicated points along the horseshoe shaped curve in FIG. 1b and with this normalization, pure monochromatic light falls at the same point along the curve irrespective of its intensity or brightness so the intensity (nominally D) must be specified separately. White light (of any intensity) falls at the point $X=0.307$ $Y=0.314$ (the point designated WL on FIG. 1b).

The light received from real objects, which is not monochromatic, fall at points within the interior of the curve. The hue or dominant "color" of such real objects is defined as the perceived color of the monochromatic light which lies at the intersection of the outer horseshoe-shaped curve with a line from the white light point (WL) through the object's location on the plot. Line WL-R is an example of this type of line and point R shows the "hue". The saturation, or chroma, of the light is a measure of how far along the line from "white" to "pure" color the object's location is found.

The hue-chroma coordinate system in FIG. 1b is irregular, however, in that the length of the vector from the center to the outer curve changes significantly with wavelength. FIG. 2 is an alternative, cylindrical coordinate system in which the hue is defined by the angular rotation from an arbitrarily chosen green-red axis, and the chroma is defined as the radial distance from the center. Here the density, or value of the light is explicitly included as the third cylindrical coordinate. The AB plane in FIG. 2 is equivalent to the XY plane in FIG. 1b.

In classic instrumental colorimetry, only the color was sought, so that the relative direction of the vector in the three dimensional space was what was important, not the amplitude. When used for color comparison, the tristimulus system outlined in conjunction with FIG. 1 reduces the dimensionality of the vector space from three to two through the use of normalization. It should be noted, however, that this self-normalized approach introduces a degree of linearization for incremental color changes which alter the three components of the xyz vector by relatively small amounts, particularly when the changes are nearly perpendicular to the starting vector itself.

These instrumental tristimulus systems do not, however, perform color vision, but rather are intended to characterize colors so they can be duplicated reliably. In particular, these systems are quite sensitive to changes in the illuminant spectrum and, hence, are not duplicating the color constancy features of mammalian color vision.

The present invention sets up an analog of visual color perception using N sources (or their equivalent) which can form a partially degenerate N-dimensional vector space. The dimensionality is preferably reduced by at least one because the vector is normalized, and perhaps by more than one because the source curves overlap strongly so that the resultant detector signals are partially correlated. Many different normalizations, such as the sum of one or more of the N signals or the length of the vector, may be used. The resultant vector space is used to characterize a higher dimensional analog of hue and chroma to quantify the amount of the "color" of glucose in the observed specimen.

FIG. 3 is a series of computer-generated simulations of the absorbance spectrum of water and sugar in the 700–1200 nm range. The locations, magnitudes, and widths of the peaks shown are taken from a variety of sources in the literature. The three indicated peaks near 1000, 920, and 840 nm appear together, for example, in the work of Koashi et al. described in U.S. Pat. No. 4,883,953, superimposed on a broad background offset. Interpretation of such reported results requires care to separate glucose spectral features from instrumental artifacts. The difficulty in obtaining reliable glucose spectra is well-known, and follows from the small magnitude of the absorption by glucose in this spectral range and from the fact that the water content and refractive index of solutions change when glucose is added. The instrumentally observed changes in detector signals in this spectral range are a mixture of increased absorbance from glucose, decreased absorbance due to the displaced water and changes in instrumental throughput due to refractive index and temperature variations during the experiments. The final result for the glucose spectrum itself is highly dependent on the accuracy of the corrections for these effects. Nevertheless, the general features shown in FIG. 3 emerge as suitably descriptive to guide the selection of detector response functions to implement the present invention.

Figure 3A:
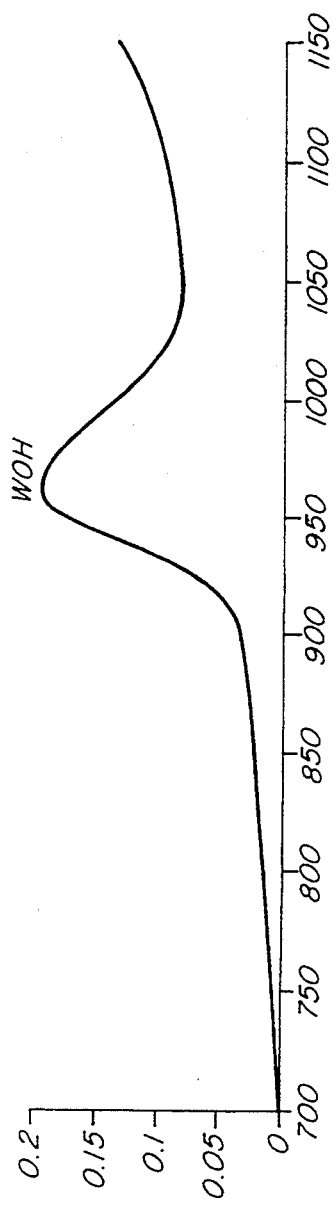
FIGS. 3a–b show computer models of water and sugar peaks plotted as absorbance versus wavelength.
Figure 3B:
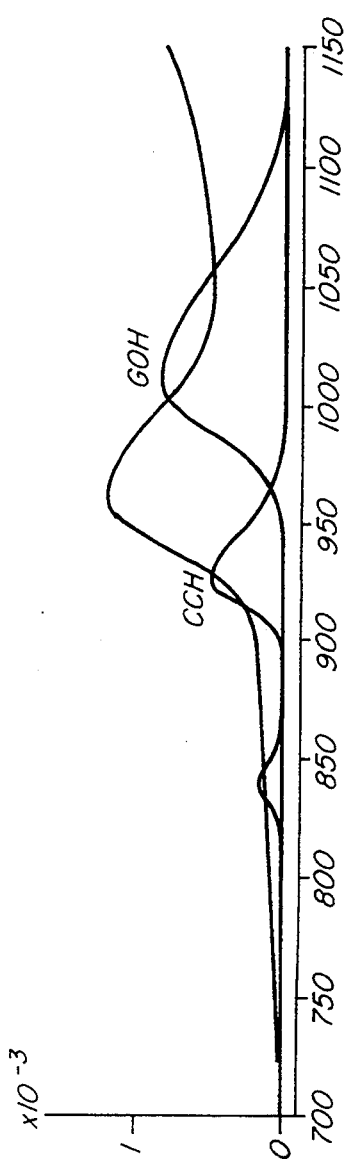

The peak (WOH) shown in FIG. 3a at 960 nm is attributed to absorption by the OH group in water. The glucose peak (GOH) near 1000 nm in FIG. 3b is also attributed to OH absorption, with its location shifted to higher wavelength as a result of local field distortions at the OH sites on the glucose due to the other atoms on the molecule. The size of the glucose peak can be readily estimated on the assumption that there is no loss of total absorbance, but only a shift. Thus, pure water is roughly 56 molar; glucose at 1 gram/dl ($=10$ grams/liter) and a molecular weight of 180 is roughly $10/180=0.056$ molar, 1000 times smaller than pure water. Each molecule of glucose, however, carries 5 OH groups: hence the glucose is roughly 0.28 molar in OH groups, and should have an absorbance about 200 times smaller than pure water. Scaling from FIG. 3a, the expected magnitude of the shifted OH peak from glucose is thus of the order of 0.001 absorbance units.

The peaks shown in FIG. 3b near 920 run (CCH) is attributed to the stretch mode of the CH bonds in glucose. Its magnitude relative to the shifted OH peak (GOH) in FIG. 3b is taken coarsely from the data presented by Koashi, as is the smaller peak at 840 nm. These three peaks are consistent with the spectral correlation plots presented by Rosenthal in U.S. Pat. No. 5,028,787, which also indicate the possible presence of another slight peak in the 750 nm range, which has not been included in FIG. 3b.

FIG. 3b also includes an estimate of the relative size of the absorbance of the water displaced by glucose at 1 gram/dl concentration. This was obtained from FIG. 3a using the tabulated specific gravity of 1.0039 (ref. Handbook of Chemistry and Physics) for such a glucose solution. Thus, if 1 gram of glucose is added to 99 grams of water, the result is 100 grams of solution filling $100/1.0039=99.61$ ml. A full deciliter of this solution then contains 99.39 grams of water (and 1.0039 grams of glucose). By comparison a full deciliter of pure water would contain 100 grams of water. Thus the change to approximately 1 gram/dl concentration of glucose reduces the water content of the solution by 0.61 grams; the magnitude of the absorbance of this displaced water is about 100/0.61 or about 164 times smaller than that of pure water.

Figure 3C:
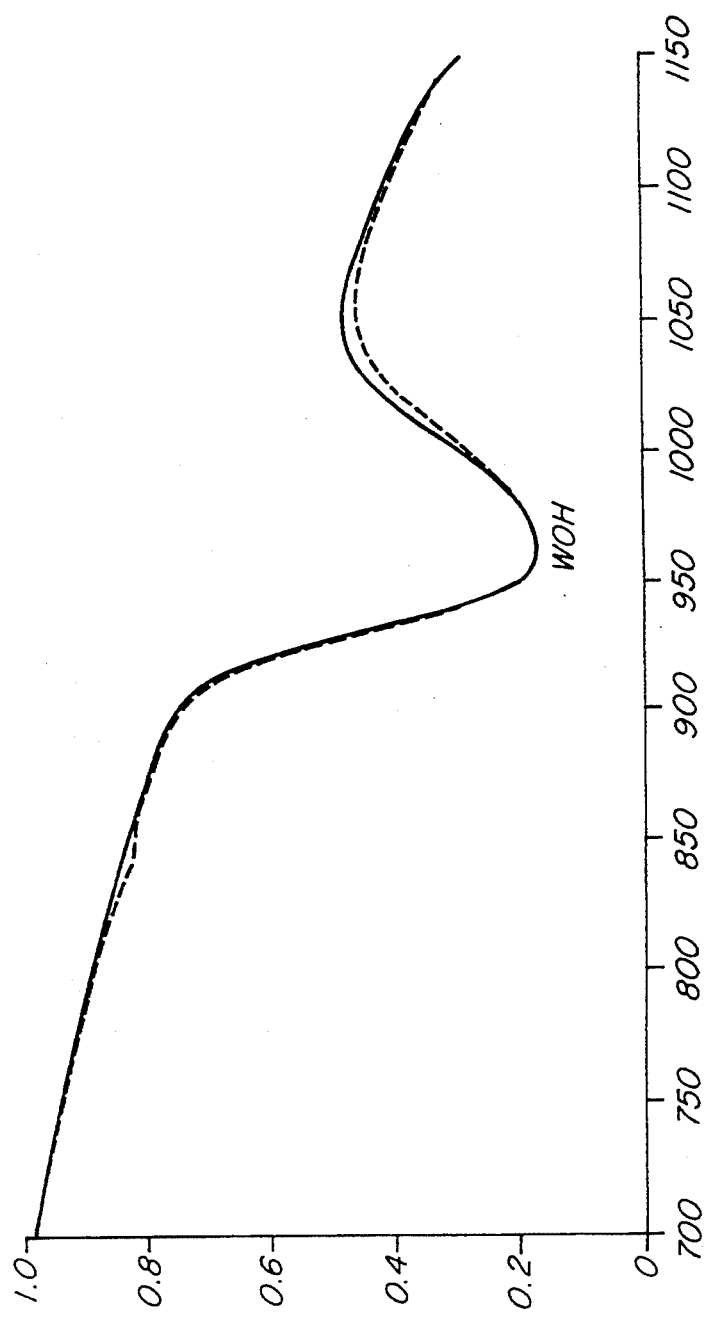
FIG. 3c shows the composite transmission spectrum of a glucose solution.

FIG. 3c shows the calculated impact of these broad and shall glucose features on the transmission spectrum of four centimeters of water. Note that the glucose concentration has been increased to 10 grams/dl to render the difference between the curves visible. The major impact of the glucose absorbance is to change the apparent shape of the 960 nm water band (WOH). The total change is slight: at the clinically significant range of 0.05–0.5 grams/dl, the changes would fall within the width of the line on the full scale plot in FIG. 3c.

The need to detect and quantify such small changes in the presence of other changes in the band shape due to temperature effects and the impact of other constituents of the fluid which may also alter the shape place a premium on making optimal use of the entire signal change due to glucose, i.e., by integrating the full change with different weights on a plurality of overlapping detectors. The information in FIG. 3 may make it possible to "tune" the filters or sources to emphasize the CH stretch and shifted OH band contribution, and diminish that from the unshifted OH band contribution, in one or more data streams, while doing the reverse in other data streams.

Figure 4:
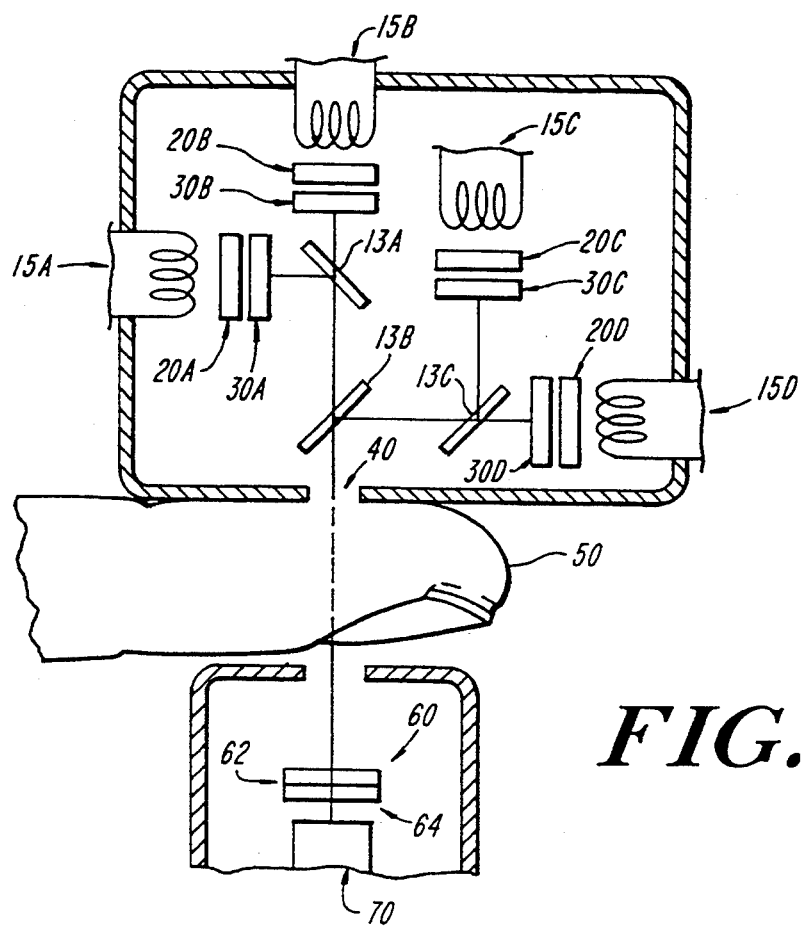
FIG. 4 is a schematic illustration of the device using a plurality of light sources and a single detector, showing congruent illumination.

FIG. 4 shows one type of apparatus particularly useful for non-invasive measurements of the concentration of a clinical analyte such as glucose using the methods of the present invention. Radiation sources 15A–15D are used to generate broad spectrum near infrared radiation (approximately 700–2500 nm). Although four sources, 15A, 15B, 15C and 15D are shown, the beams they generate may be derived from a single source using beam splitters. Sources 15 (and beam splitters 13 used to direct the radiation) are preferably spaced such that congruent illumination is achieved; that is, the pathlength and angles from any of sources 15 to the sample are equal and each source is superimposible with any other. One possible light source is a tungsten-halogen bulb in a quartz envelope, filtered, if necessary, to provide only the 700–2500 nm wavelength range. One or more source reference detectors 12, on each source, or, optionally, on the single originating source, may be used both to measure the near infrared "color" of the source and to guard against any changes in source output.

Choppers 20, illustrated as 20A, 20B, 20C and 20D, are used to temporarily modulate output of sources 15 A–D, each at a different frequency. Any other coding or modulating means which provides a form of temporally differential "fingerprint" on each beam could be used. The frequencies of modulation are chosen so as to allow discrimination in the detection stage both among the radiation from each of the sources and from any radiation originating external to the apparatus; for example, radiation entering the apparatus at the sample chamber opening allowing for sample insertion and removal. Normally, at least kilohertz frequencies of modulation can be used.

Filters 30, illustrated as filters 30A, 30B, 30C and 30D, are broad bandpass infrared filters, with spectral responses centered on different wavelengths in the near infrared. These filters allow passage of radiation in mutually overlapping regions of the spectrum. A filter is provides for each of the sources. Although the filters are shown as following the chopper, in many embodiments the filters precede the chopper.

Figure 5:
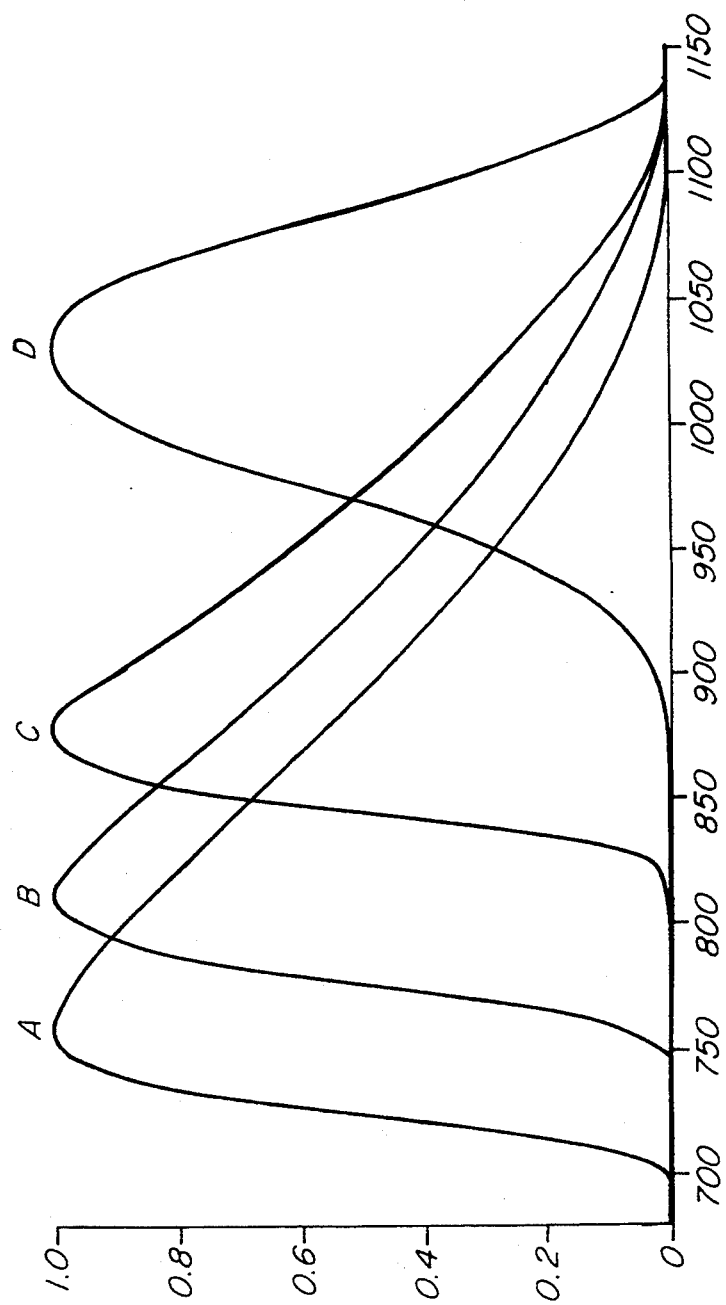
FIG. 5 is a plot of relative spectral response versus wavelength for a filter set.

FIG. 5 shows the relative intensities of the outputs of a possible set of filters useful in the invention as a function of the wavelength of incident radiation. It will be understood by those skilled in the art that the particular wavelengths and relative intensities shown in FIG. 5 are not of unique significance, so that different embodiments of the invention may have somewhat different filter response functions. Each of the four response curves is a composite of the spectral response of the silicon detector (HAMMATSU S2387 Series) and the transmission of at least one 3 mm thick Schott glass filter. If a pair of filters is used (as in filter sets A, B and C), filters are in series. In each of case A, B and C, the first illuminated filter in the pair is a long-pass filter whose transmission rises with increasing wavelength (RG9, RG780, RG850, respectively). The second filter, made of KG2 glass, acts as a short-pass filter whose transmission falls with increasing wavelength. For the D detector, a single filter such as a RG1000 filter is used and the decrease in response at the highest wavelengths is produced by the spectral response of the silicon detector itself.

In another embodiment, sources 15 and filters 30 can be eliminated and replaced by LED's which have broadband, overlapping emissions. Choppers 20 can be used to modulate the output of the LED's, but turning the LED's on and off electrically is an easier modulation method.

Figure 6:
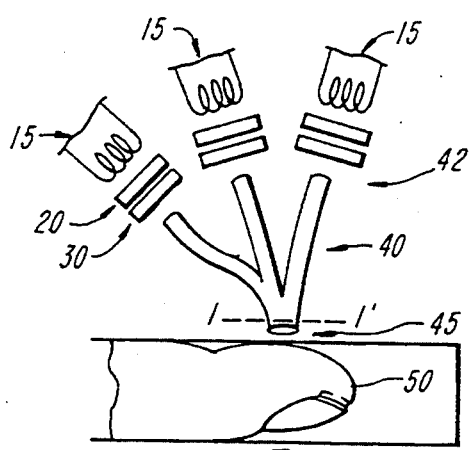
FIG. 6 is a schematic illustration of the device using a fiber optic bundle to provide congruent illumination from a plurality of radiation sources.
Figure 7:
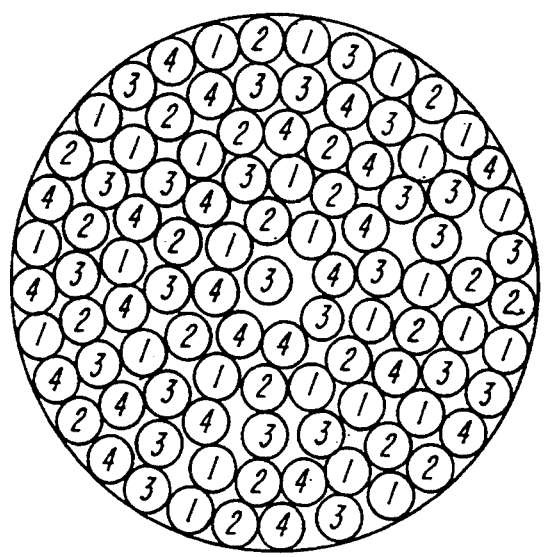
FIG. 7 is a detail of the fiber optic cable at a line 1—1 from FIG. 6.

Illumination from the sources 15, as filtered and modulated, is transmitted to the sample through transmission means 40 such as a lens and/or an aperture. In another embodiment, shown in FIGS. 6 and 7, transmission means 40 is shown as a bundle of optical fibers. At one end 42, the bundle is branched so as to admit radiation separately transmitted by each of the sets of sources 15, choppers 20, and filters 30. In the trunk of the bundle 45, the fibers originating from the various beams are randomly distributed so that the foot of the fiber 48 transmits radiation which is substantially uniformly distributed. FIG. 7 shows a cross-section of bundle 40 along line 1—1. This transmitted radiation is comprised of that transmitted by the various filters. This form of bundle could also be used with LED sources.

A sample containing the constituent of interest is inserted in sample chamber 50. The chamber may be arranged for insertion and removal of a body part, such as a finger. If a non-body sample, such as an agricultural sample, is to be tested, a sample chamber of the appropriate shape may be used in the same location. Because the infrared radiation generated by the "color-producing" filters 15 has been coded by the choppers, any extraneous radiation admitted into the chamber will not result in erroneous measurements; that is, the extraneous radiation does not carry the same coded or modified information.

The radiation transmitted (or reflected) by the sample passes to detector 60. Detector 60 includes a silicon photocell detector 62, placed on the side of the sample chamber directly opposite the foot of transmission means 40. Optionally, an aperture and an appropriate number of beam splitters may be placed between the sample and the detector array to ensure that radiation impinges on all the detectors at equal angles and after traveling equal path lengths so as to eliminate sample-independent variations in the detected intensity, thereby achieving coherent sampling. Alternatively, detector 60 may have a detector array substituted for the single photocell detector 62, with the individual elements of the array spatially displaced so that each element samples the light emerging from a different point on the sample. The array is positioned so that its elements receive light from different paths through the tissue which have different background induced changes in the effective illumination. This arrangement facilitates the separation of the relatively constant analyte concentration from the highly variable background changes in illuminant.

Detector 60 also includes a decoder 64 responsive to the modulation of the radiation transmitted to the detector from choppers 20. For example, decoder 64 selectively amplifies only those signals detected by the detector array 62 which are modulated at one of the modulation frequencies determined by the choppers 20 A–D. Narrow bandpass electric filters are preferred decoders 64. Thus, detector 60 in effect simultaneously detects and decodes the radiation transmitted or reflected by the sample in sample chamber 50.

The output from decoder 64 is fed to analysis means 70, which may be a computer, hard-wired logic circuits, or a neural network. In any case, analysis means 70 converts the output signal from the detectors to a measure of the concentration of the analyte of interest.

Analysis means 70 may treat the data received from detector 60 in a variety of ways. For example, an analog of colorimetric tristimulus values can be produced and compared to a previous calibration against known glucose concentrations; e.g., stored reference values. Problems that may arise with this simple type of data analysis include the requirement for frequent calibration because if the calibration is not sufficiently universal, it will lack the analog of "color constancy." This deviation from ideal measurement plagues all classic colorimeters.

Data analysis can be improved to more closely approach color perception of the eye and brain by digital computation or with the use of neural networks. While artificial neural networks usually contain hundreds of interconnected neurons, this analog of color perception may only require about two dozen. The artificial neural network attempts to simulate visual signal processing by the neurons of the eye, the optic nerve, and the brain. The neural network is configured to achieve the infrared equivalent of color constancy by combining the "tristimulus" information from detector 60 with stored, previously determined, reference signals, or with signals derived from paired detectors with reference generating signal elements. In the case that detector 60 incorporates the non-congruent array of detector elements, color constancy is obtained by intercomparing the "tristimulus" readings on the different array elements. Alternatively, a combination of all these referencing methods may be used to achieve color constancy for the analyte of interest.

An important advantage offered by using a neural network as part of analysis means 70 is the network's capacity to learn. Because of this capacity, a network may require only a single calibration per individual subject, or may even allow for universal calibration at the factory, and still give consistent results over time.

Figure 8:
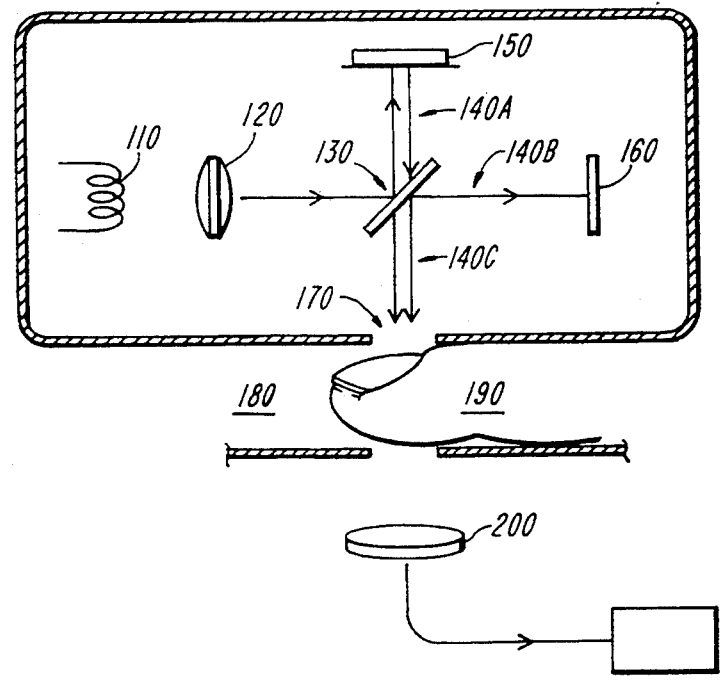
FIG. 8 is a schematic of the interferometer version of the present invention.

FIG. 8 shows another embodiment of the invention, one using interferometer as the illuminating source. More particularly, FIG. 8 shows an interferometer 100 having a lamp 110 which generates radiation that passes through collimating lens 120 before it hits beam splitter 130. At beam splitter 130, the beam is split into two parts, beams 140A and 140B. Beam 140A strikes fixed mirror 150 while beam 140B is directed to moving mirror 160. Beams 140A and 140B are reflected by mirrors 150 and 160, respectively, and recombine on the output side of beam splitter 130 to form a new beam 140C. As moving mirror 160 sweeps, the pathlength difference between beams 140A and 140B changes by many wavelengths of light. Beams 140A and 140B interfere coherently and produce a sinusoidal variation of intensity with time on beam 140C, at a different electrical frequency for each wavelength of incident light. Beam 140C, which contains a multitude of wavelengths each with its own interference pattern at its own frequency, passes through launch aperture 170 into sample chamber 180 and through sample 190. The beam transmitted by sample 190 goes to detector 200, which includes broadpass electrical filters and integrators for generating a signal substantially similar to that generated by the apparatus shown in FIG. 4 which is then passed to the analysis means as previously described. This signal is analyzed using the analysis means such as a computer and/or a neural net to generate the requisite information.

The foregoing description invention is only meant to be explanatory and is not intended to limit the scope of the invention. The invention is defined by the following claims.

What is claimed is:

1. An apparatus for determining the concentration of a constituent of interest in a sample which has absorbance or reflectance in a selected region of the spectrum comprising:
    radiation generating means which generates a plurality of beams of radiation in a selected region of the spectrum;
    coding means for placing an identifiable, distinct code on each of said plurality of beams of radiation;
    filtering means for individually optically filtering each of said plurality of beams such that each of said beams is limited in wavelength to a distinct portion of said selected region of said spectrum, the portion of the spectrum for which each of said beams is limited having at least a partial overlap with the portion of the spectrum for at least one other beam;
    transmission means for transmitting said coded beams to illuminate said sample;
    a sample chamber for confining said sample during illumination;
    detection means for detecting the intensity of radiation transmitted or reflected by said sample, said detection means including decoding means for identifying the code on each of said coded beams, said detection means generating an output signal which is a function of the information carried by each coded beam; and
    analysis means for converting said output signal into a measure of said concentration of said constituent of interest in said sample.

2. The apparatus of claim 1 wherein said selected region of said spectrum comprises 700–2500 nm.

3. The apparatus of claim 1 wherein said radiation generation means comprise a radiation source and beam splitters splitting the radiation emitted by said radiation source into said plurality of beams.

4. The apparatus of claim 1 wherein said radiation generation means comprise a plurality of separate radiation sources.

5. The apparatus of claim 1 wherein said plurality of separate beams provide congruent illumination.

6. The apparatus of claim 1 wherein said coding means individually temporally modulates the intensity of said beams.

7. The apparatus of claim 6 wherein said coding means comprises a chopper associated with each of said beams.

8. The apparatus of claim 1 wherein said filtering means comprises a plurality of broad bandpass filters, each said filters having a spectral transmission centered about a separate portion of said selected region of the spectrum, said portion of spectral transmission for each filter partially overlapping that of at least one other filter.

9. The apparatus of claim 1 wherein said transmission means comprise a plurality of optical fibers, one end of each of said plurality of fibers admitting radiation from one of said beams, the other ends of said fibers being randomly distributed in a bundle so as to uniformly distribute said beams to illuminate said sample.

10. The apparatus of claim 9 wherein said radiation generation means and said plurality of optical fibers are arranged to provide congruent illumination.

11. The apparatus of claim 6 wherein said decoding means comprises electrical narrow bandpass filters substantially centered about the temporal frequency of modulation.

12. The apparatus of claim 2 wherein said analysis means generates an output which corresponds to a location in a multi-dimensional space, said multi-dimensional space being an analog of a colorimetric space in the visible region.

13. The apparatus of claim 1 wherein said analysis means comprises an artificial neural network.

14. The apparatus of claim 1 wherein said detection means is selected from the group consisting of silicon photocells and lead selenide cells.

15. The apparatus of claim 1 wherein said sample chamber is arranged for non-invasive measurements on a portion of a human body.

16. The apparatus of claim 15 wherein said human body portion comprises a finger.

17. The apparatus of claim 15 wherein said constituent of interest is an analyte of clinical interest.

18. The apparatus of claim 17 wherein said constituent of interest is selected from the group consisting of glucose and glucose indicating constituents.

19. The apparatus of claim 17 wherein said constituent of interest is selected from the group consisting of drugs of abuse, drugs of abuse indicating constituents, alcohol, hemoglobin and its variants, cholesterol and lipids.

20. The apparatus of claim 1 wherein said detection means comprises an array of detectors.

21. The apparatus of claim 20 wherein said array of detectors are arranged to provide congruent sampling.

22. The apparatus of claim 20 wherein said array of detectors are arranged so that incongruent sampling is effected and said analysis means comprises means to compare said plurality of decoded signals in order to generate an information signal indicative of said concentration of said constituent of interest while rendering the interfering features of the backgrounds from each of said detectors in the array to be less distinct than the backgrounds are in any of the individual detector's signals.

23. The apparatus of claim 1 wherein a portion of at least one of said beams is directed through a reference material to an additional detector to generate reference values which can be used to correct for color constancy.

24. The apparatus of claim 23 wherein said plurality of beams are congruently combined before said portion of any beam is directed to said reference material.

25. The apparatus of claim 1 wherein stored reference values are used to correct for color constancy.

26. The apparatus of claim 1 wherein paired detectors are used to provide congruent sampling.

27. A method of measuring the concentration of a constituent of interest in a sample which has absorbance or reflectance in a selected region of the spectrum comprising the steps of:
   illuminating said sample with a plurality of beams of radiation, each of said beams being limited in wavelength to a distinct portion of said selected spectral region, with each of said distinct spectral portions having at least partial overlap in wavelength with the distinct spectral portion of at least one other of said beams, each of said beams also having an identifiable code associated therewith which is distinct from the code of any other of said beams;
   detecting transmitted or reflected radiation from said sample;
   decoding said identifiable code from each of said beams to generate a signal indicative of said detected radiation; and
   analyzing said signals to measure the concentration of said constituent of interest.

28. The method of claim 27 wherein the code associated with each of said beams comprises a distinct and identifiable modulation.

29. The method of claim 28 wherein said modulation comprises temporally modulating the intensity of said beams.

30. The method of claim 29 wherein said temporal modulation is achieved using choppers.

31. The method of claim 27 wherein said plurality of partially overlapping portions of the spectrum lie between 700–2500 nm.

32. The method of claim 30 wherein said detecting and said decoding steps generate signals which are analogs of the signals generated by the retinal cones.

33. The method of claim 32 wherein said analysis step generates an output which is an analog of a location in a colorimetric multi-dimensional space.

34. The method of claim 27 wherein said analysis means comprises an artificial neural network.

35. The method of claim 27 wherein said method is used for non-invasive testing for a constituent in a human body.

36. The method of claim 35 wherein said sample comprises a finger.

37. The method of claim 35 wherein said constituent of interest is an analyte of clinical interest.

38. The method of claim 37 wherein said constituent of interest is selected from the group consisting of drugs of abuse, drugs of abuse indicating constituents, alcohol, hemoglobin and its variants, cholesterol and lipids.

39. The method of claim 37 wherein said constituent of interest is selected from the group consisting of glucose and glucose-indicating constituents.

40. The method of claim 27 wherein said illumination step comprises congruent illumination.

41. The method of claim 27 wherein said detection step is carried out by an array of detectors arranged to provide congruent sampling.

42. The method of claim 27 wherein said detection step is carried out by an array of detectors arranged to provide incongruent sampling, wherein the decoded signals from said detectors are mixed and recombined to create a color constant measure of the concentration of said constituent of interest which includes correction for changes in effective illumination.

43. The method of claim 27 wherein a portion of at least one of said beams is directed through a reference material to an additional detector to generate reference values which can be used to correct for color constancy.

44. The method of claim 43 wherein said plurality of beams are congruently combined before said portion of any beam is directed to said reference material.

45. The method of claim 27 wherein stored reference values are used to correct for color constancy.

46. The method of claim 27 wherein paired detectors are used to provide congruent sampling.

47. An apparatus for determining the concentration of a constituent of interest in a sample which has absorbance or reflectance in a selected region of the spectrum comprising:
   a plurality of LED's each of which generate a beam of radiation in a selected region of the spectrum, each of said beams having at least partial overlap in wavelength with at least one other of said beams;
   coding means for placing a separate and identifiable, distinct code on each of said beams of radiation;
   transmission means for transmitting said coded beams to illuminate said sample;
   a sample chamber for confining said sample during illumination;
   detection means for detecting the intensity of radiation transmitted or reflected by said sample, said detection means including decoding means for identifying the code on each of said coded beams, said detection means generating an output signal which is a function of the information carried by each coded beam; and
   analysis means for converting said output signal into a measure of said concentration of said constituent of interest in said sample.

48. The apparatus of claim 47 wherein said selected region of said spectrum comprises 700–2500 nm.

49. The apparatus of claim 47 wherein said coding means individually temporally modulates the intensity of said beams.

50. The apparatus of claim 49 wherein said coding means comprises a means for turning said LED's on and off to generate the code associated with each of said beams.

51. The apparatus of claim 47 wherein said plurality of LED's are physically arranged to provide congruent illumination.

52. The apparatus of claim 47 wherein said transmission means comprise a plurality of optical fibers, one end of each of said plurality of fibers admitting radiation from one of said beams, the other ends of said fibers being randomly distributed in a bundle so as to uniformly distribute said beams to illuminate said sample.

53. The apparatus of claim 52 wherein said LED's and said plurality of optical fibers are arranged to provide congruent illumination.

54. The apparatus of claim 49 wherein said decoding means comprises electrical narrow bandpass filters substantially centered about the temporal frequency of modulation.

55. The apparatus of claim 48 wherein said analysis means generates an output which corresponds to a location in a multi-dimensional space, said multi-dimen-

21 sional space being an analog of a colorimetric space in the visible region.

56. The apparatus of claim 47 wherein said analysis means comprises an artificial neural network.

57. The apparatus of claim 47 wherein said detection means is selected from the group consisting of silicon photocells and lead selenide cells.

58. The apparatus of claim 47 wherein said sample chamber is arranged for non-invasive measurements on a portion of a human body.

59. The apparatus of claim 58 wherein said human body portion comprises a finger.

60. The apparatus of claim 58 wherein said constituent of interest is an analyte of clinical interest.

61. The apparatus of claim 60 wherein said constituent of interest is selected from the group consisting of glucose and glucose indicating constituents.

62. The apparatus of claim 60 wherein said constituent of interest is selected from the group consisting of drugs of abuse, drugs of abuse indicating constituents, alcohol, hemoglobin and its variants, cholesterol and lipids.

63. The apparatus of claim 47 wherein said detection means comprises an array of detectors.

64. The apparatus of claim 63 wherein said array of detectors are arranged to provide congruent sampling.

65. The apparatus of claim 47 wherein said array of detectors are arranged so that congruent sampling is effected and said analysis means comprises means to compare said plurality of decoded signals in order to generate an information signal indicative of said concentration of said constituent of interest while rendering the interfering features of the backgrounds from each of said detectors in the array to be less distinct than the backgrounds are in any of the individual detector's signals.

66. The apparatus of claim 47 wherein a portion of at least one of said beams is directed through a reference material to an additional detector to generate reference values which can be used to correct for color constancy.

67. The apparatus of claim 66 wherein said plurality of beams are congruently combined before said portion of any beam is directed to said reference material.

68. The apparatus of claim 47 wherein stored reference values are used to correct for color constancy.

69. The apparatus of claim 47 wherein paired detectors are used to provide congruent sampling.

70. A method of measuring the concentration of a constituent of interest in a sample which has absorbance or reflectance in a selected region of the spectrum comprising the steps of:

illuminating said sample with a plurality of beams of radiation, each of said beams being generated by LED's which are limited in wavelength to a distinct portion of said selected spectral region, with each of said distinct spectral portions having at least partial overlap in wavelength with the distinct spectral portion of at least one other of said beams, each of said beams also having an identifiable code associated therewith which is distinct from the code of any other of said beams;

detecting transmitted or reflected radiation from said sample;

decoding said identifiable code from each of said beams to generate a signal indicative of said detected radiation from each of said beams; and

22 analyzing said signals to measure the concentration of said constituent of interest.

71. The method of claim 70 wherein the code associated with each of said beams comprises a distinct and identifiable modulation.

72. The method of claim 71 wherein said modulation comprises temporally modulating the intensity of said beams.

73. The method of claim 72 wherein said temporal modulation is achieved by turning the LED's on and off at the modulation frequency.

74. The method of claim 70 wherein said plurality of partially overlapping portions of the spectrum in said spectral region lie between 700–2500 nm.

75. The method of claim 74 wherein said detecting and said decoding steps generate signals which are analogs of the signals generated by the retinal cones.

76. The method of claim 74 wherein said analysis means generates an output which is an analog of a location in a colorimetric multi-dimensional space.

77. The method of claim 70 wherein said analysis means comprises an artificial neural network.

78. The method of claim 70 wherein said method is used for non-invasive testing for a constituent in a human body.

79. The method of claim 78 wherein said sample comprises a finger.

80. The method of claim 78 wherein said constituent of interest is an analyte of clinical interest.

81. The method of claim 80 wherein said constituent of interest is selected from the group consisting of drugs of abuse, drugs of abuse indicating constituents, alcohol, hemoglobin and its variants, cholesterol and lipids.

82. The method of claim 80 wherein said constituent of interest is selected from the group consisting of glucose and glucose-indicating constituents.

83. The method of claim 70 wherein said illumination step comprises congruent illumination.

84. The method of claim 70 wherein said detection step is carried out by an array of detectors arranged to provide congruent sampling.

85. The method of claim 70 wherein said detection step is carried out by an array of detectors arranged to provide incongruent sampling, wherein the decoded signals from said detectors are mixed and recombined to create a color constant measure of the concentration of said constituent of interest which includes correction for changes in effective illumination.

86. The method of claim 70 wherein a portion of at least one of said beams is directed through a reference material to an additional detector to generate reference values which can be used to correct for color constancy.

87. The method of claim 86 wherein said plurality of beams are congruently combined before said portion of any beam is directed to said reference material.

88. The method of claim 70 wherein stored reference values are used to correct for color constancy.

89. The method of claim 70 wherein paired detectors are used to provide congruent sampling.

90. An apparatus for performing colorimetry or an analog of colorimetry using absorption or reflectance of radiation in a selected portion of the spectrum comprising:

radiation generation means generating a plurality of broad wavelength beams of radiation in said selected region of the spectrum;

coding means for producing a distinct, identifiable code associated with each of said beams;

optical filtering means in the form of a plurality of broad bandpass filters, each said filter having a spectral transmission centered about a separate portion of said selected radiation, the spectral transmission for each filter partially overlapping that of at least one other filter;

detection means differentially responsive to said coded beams, said response being in the form of an output signal which is a function of the information carried by said coded beams; and analysis means for converting said output into the colorimetry or analog of colorimetry values.

91. The apparatus of claim 90 wherein said selected region of the spectrum comprises 700–2500 nm.

92. The apparatus of claim 90 wherein said coding comprises temporal modulation of the intensity of said beams.

93. The apparatus of claim 90 wherein said analysis is carried out using a neural net.

94. The apparatus of claim 90 wherein a portion of at least one of said beams is directed through a reference material to an additional detector to generate reference values which can be used to correct said colorimetry or analog of colorimetry values for color constancy.

95. The apparatus of claim 94 wherein said plurality of beams are congruently combined before said portion of any beam is directed to said reference material.

96. The apparatus of claim 90 wherein stored reference values are used to correct for color constancy.

97. The apparatus of claim 90 wherein paired detectors are used to provide congruent sampling.

98. A method for performing colorimetry or an analog of colorimetry using transmission or reflectance measurements comprising the steps of:

illuminating a sample with a plurality of beams of radiation, each of said beams being centered about a different portion of a selected region of the spectrum and partially overlapping spectrally with the portion of at least one other beam;

detecting transmitted or reflected radiation from said sample;

generating at least one signal corresponding to said detected radiation; and analyzing said signal to convert it to the colorimetry or analog of a colorimetry value;

wherein each of said beams is distinguishably coded with an identifying code prior to impinging on the sample and is decoded subsequent to impinging on the detector.

99. The method of claim 98 wherein said selected region of the spectrum comprises 700–2500 nm.

100. The method of claim 98 wherein said coding comprises temporal modulation of the intensity of each of said beams.

101. The method of claim 98 wherein a portion of at least one of said beams is directed through a reference material to an additional detector to generate reference values which can be used to correct said colorimetry or analog of colorimetry values for color constancy.

102. The method of claim 101 wherein said plurality of beams are congruently combined before said portion of any beam is directed to said reference material.

103. The method of claim 98 wherein stored reference values are used to correct for color constancy.

104. The method of claim 98 wherein paired detectors are used to provide congruent sampling.

105. An apparatus for performing colorimetry or an analog of colorimetry using absorption or reflectance of radiation in a selected portion of the spectrum comprising:

a plurality of LED's each emitting a broad wavelength beam of radiation in said selected region of the spectrum, the spectral emission for each LED partially overlapping that of at least one other LED;

coding means for producing a distinct, identifiable code associated with each of said beams;

detection means differentially responsive to said coded beams, said response being in the form of an output signal which is a function of the information carried by said coded beams; and analysis means for converting said output into the colorimetry or analog of colorimetry values.

106. The apparatus of claim 105 wherein said selected region of the spectrum comprises 700–2500 nm.

107. The apparatus of claim 105 wherein said coding comprises temporal modulation of the intensity of said beams.

108. The apparatus of claim 105 wherein said analysis is carried out using a neural net.

109. The apparatus of claim 105 wherein a portion of at least one of said beams is directed through a reference material to an additional detector to generate reference values which can be used to correct said colorimetry or analog of colorimetry values for color constancy.

110. The apparatus of claim 109 wherein said plurality of beams are congruently combined before said portion of any beam is directed to said reference material.

111. The apparatus of claim 105 wherein stored reference values are used to correct for color constancy.

112. The apparatus of claim 105 wherein paired detectors are used to provide congruent sampling.

113. An apparatus for determining the concentration of a constituent of interest in a sample which has absorbance or reflectance in a selected region of the spectrum comprising:

radiation generating means which generates a beam of broad spectrum radiation;

coding means for placing a distinct, identifiable frequency of modulation on each of the wavelengths in said beam of radiation;

transmission means for transmitting said coded beams to illuminate said sample;

a sample chamber for confining said sample during illumination;

detection means for detecting the intensity of radiation transmitted or reflected by said sample, said detection means including filtering means for electronically filtering said reflected or transmitted radiation, said filtering means comprising a plurality of electrical broad bandpass filters each having a frequency transmission centered about a selected portion of the frequencies of modulation of the wavelengths, each of said selected portions transmitted by said electronic broad bandpass filters having at least a partial overlap with the portion of the selected region for at least one other electronic broad bandpass filter, said detection means generating an output signal which is a function of the information carried by said coded wavelengths; and analysis means for converting said output signal into a measure of said concentration of said constituent of interest in said sample.

114. The apparatus of claim 113 wherein said analysis means comprises an integrator to integrate the output of the each of said electric broad bandpass filters.

115. The apparatus of claim 113 wherein said radiation generating means and said coding means comprise a scanning interferometer.

* * * * *